US005858375A

United States Patent [19]

Furminger et al.

[11] Patent Number: 5,858,375

[45] Date of Patent: Jan. 12, 1999

[54] PHARMACEUTICAL COMPOSITIONS CONTAINING $D_2O$

[75] Inventors: Ian George Stephen Furminger; Philip James Sizer, both of Leatherhead, United Kingdom

[73] Assignee: Medeva Europe Limited, United Kingdom

[21] Appl. No.: 793,292

[22] PCT Filed: Sep. 15, 1995

[86] PCT No.: PCT/GB95/02190

§ 371 Date: May 21, 1997

§ 102(e) Date: May 21, 1997

[87] PCT Pub. No.: WO96/08273

PCT Pub. Date: Mar. 21, 1996

[30] Foreign Application Priority Data

Sep. 15, 1994 [GB] United Kingdom .................. 9418609

[51] Int. Cl.[6] .......................... A61K 39/13; A61K 39/12

[52] U.S. Cl. .................................... 424/217.1; 424/204.1

[58] Field of Search .............................. 424/207.1, 217.1

[56] References Cited

FOREIGN PATENT DOCUMENTS

| | | |
|---|---|---|
| 0332826 A1 | 1/1989 | European Pat. Off. . |
| 0568726 A2 | 8/1992 | European Pat. Off. . |
| A 244492 | 4/1987 | Germany . |
| WO A 9421298 | 9/1994 | WIPO . |

OTHER PUBLICATIONS

Jenson et al., *Diagn. Microbiol. Infect. Dis.,* vol. 19, pp. 137–142, 1994.

WPI Acc. No. 94–307582/38 & JP–624659 (ZH–Handai Biseibutsubyok) 23 Aug. 1994.

Bovarnick et al, J. Bacteriology 59:509–22, 1950, "The Influence of Certain Salts, Amino Acids, Sugars, and Proteins on the Stability of Rickettsiae".

Zanella et al, (1973) Avian Pathology Vo. 3, No. 1, 15–24, "Lyophilized Turkey Herpesvirus (HVT): Stability of Vaccine and Minimum Protective Dose".

Patrasau et al, (1971), "In Vitro Assay of Cell–Free Turkey Herpesvirus".

Calnek et al, (1970), Applied Microbiology 20, 723–726, "Lyophilization of Cell–Free Marek's Disease Herpesvirus and a Herpesvirus from Turkey".

Nicholas et al (1977) Journal of Biological Standardisation 5, 333–339, "The Stability of Reconstituted Marek's Disease Vaccines".

Science News, vol. 145, Iss:n22, May 28, 1994, p. 344(2), ISSN:0036–8423.

Poliomyelitis Vaccines, entry 7992–e, p. 1173.

Wu et al (1995) Vaccine 13, 1058–1063.

*Primary Examiner*—Toni R. Scheiner
*Attorney, Agent, or Firm*—Nixon & Vanderhye

[57] ABSTRACT

A pharmaceutical composition comprises a solution or suspension of a biological agent in a diluent comprising $D_2O$, which solution or suspension contains sufficient amounts of a sugar, phosphate, glutamic acid or a physiologically acceptable salt thereof and, optionally, a non-toxic protein, a peptone or a mixture of two or more amino acids besides glutamic acid to enhance the stability of the agent. Typically, the composition is a suspension of a live attenuated poliovirus or an inactivated poliovirus of each of poliovirus types 1, 2 and 3. Preferably the solution or suspension contains stabilising amounts of sucrose, $KH_2PO_4$, $K_2HPO_4$, L-glutamic acid or sodium glutamate and human serum albumin (SPGA).

12 Claims, 1 Drawing Sheet

GRAPHS OF MEAN $LOG_{10}$ TITRE AT DAY 0 AND DAY 7

NO STABILISER

SPGA

MgC12

PHARMACEUTICAL COMPOSITIONS CONTAINING $D_2O$

The present invention relates to stabilised pharmaceutical compositions and to their preparation.

Biological agents such as proteins, nucleic acids and live attenuated or inactivated viruses can be formulated in a number of ways for pharmaceutical use. They may be formulated as aqueous solutions or dispersions. Such solutions or dispersions should, however, have a shelf-life of several months or, better, a year or more to take account of the time that may elapse between manufacture and use.

It is impossible to store solutions or dispersions of many biological agents at room temperature for prolonged periods of time without deterioration. This problem is overcome in some instances by freeze-drying to form a lyophilisate. The lyophilisate then has to be reconstituted prior to use which can itself be a difficulty. Alternatively, solutions or dispersions may be stored at a reduced temperature such as in a refrigerator in order to reduce degradation.

We have now found that solutions or dispersions of biological agents can be better stabilised by using deuterium oxide as the principal diluent in combination with a number of other components. Especially, live virus vaccines can be better stabilised.

Accordingly, the present invention provides a pharmaceutical composition which comprises a solution or suspension of a biological agent in a diluent comprising $D_2O$, which solution or suspension contains sufficient amounts of a sugar, phosphate, glutamic acid or a physiologically acceptable salt thereof and, optionally, a non-toxic protein, a peptone or a mixture of two or more amino acids besides glutamic acid to enhance the stability of the agent.

The invention can be applied to biological macromolecules such as proteins and nucleic acids. It may be applied to recombinant proteins. The proteins may be cytokines, enzymes or antibodies such as interferons, interleukins, antigens and enzymes. The protein may be erythropoetin, blood clotting factor VIII, insulin, human growth hormone or another growth factor. The nucleic acid may be DNA or RNA.

The invention can also be applied to viruses, in particular to live attenuated or inactivated viruses. Such viruses may be used in vaccines. They are not therefore virulent. The invention is particularly applicable to live virus vaccines.

The virus may be a RNA virus or a DNA virus. The virus may be influenza virus or poliovirus. The invention can thus be applied to live attenuated or inactivated poliovirus types 1, 2 or 3. A preferred composition of the invention is a suspension of a live attenuated poliovirus or of an inactivated poliovirus of each of poliovirus types 1, 2 and 3.

Any vaccine strain of poliovirus may be employed. The strain may therefore be a Sabin strain type 1, 2 or 3 poliovirus. Sabin strains are live attenuated polioviruses. Further, attenuated polioviruses can be constructed by genetic mutation, for example by genetic mutation of the 5' non-coding region of the poliovirus genome. Alternatively, the invention can be applied to Salk type 1, 2 and 3 polioviruses. Salk vaccines are poliovirus vaccines containing inactivated poliovirus.

The sugar in the pharmaceutical composition of the invention is typically a mono-, di-saccharide or tri-saccharide such as glucose, fructose, sucrose, lactose, maltose or cellobiose Preferably it is sucrose.

The phosphate is typically an orthophosphate. It may be potassium dihydrogen orthophosphate, $KH_2PO_4$, and/or dipotassium hydrogen orthophosphate, $K_2HPO_4$. The phosphate can act as a buffer, for example to ensure that a solution or suspension according to the invention has a pH of from 6.2 to 7.2 such as from 6.5 to 7.0.

Preferably the glutamic acid is L-glutamic acid. The preferred salt is the monosodium salt.

The optional non-toxic protein, peptone or mixture of two or more amino acids other than glutamic acid is generally albumin. The albumin can be bovine serum albumin or preferably human serum albumin.

The biological agent is dissolved or dispersed in a diluent comprising $D_2O$. The diluent thus consists essentially of $D_2O$. $D_2O$ is the principal diluent. Minor amounts of other physiologically acceptable diluents miscible with $D_2O$ may be present, typically $H_2O$. For example, another diluent such as $H_2O$ may be present in an amount of up to 30%, for example up to 20%, by weight of the composition; for example from 1, or from 5, to 10, or to 15%, by weight.

The amount of the biological agent varies depending upon the nature of the agent and the desired final concentration of the agent. The agent may be present in the pharmaceutical composition of the invention in an amount of from 1 to 20% by weight, for example from 5 to 10% by weight.

In the case of viruses, the amount present may be represented by a titre. A suitable titre may therefore be from $10^{6.5}$ to $10^{7.5}$ per ml, for example $10^{6.8}$ to $10^{7.2}$ per ml and more especially about $10^{6.9}$ per ml. Such titres are particularly appropriate in the case of a poliovirus.

An advantage of the present invention is that less of an active agent may be provided in a composition than would otherwise be the case. An excess or "overage" of an agent may be initially provided in a composition to take account of degradation of the active agent in the period of time between manufacture of the composition and use. As the present compositions exhibit enhanced stability, this overage can be reduced.

The amount of $D_2O$ in the composition may vary depending upon, for example, the amount of biological agent that is present. Typically the amount of $D_2O$ is from 70 to 95% by weight of the composition, for example from 75 to 90% or from 75 to 85%. The $D_2O$ itself has an effect in increasing the stability of the compositions of the invention.

Sufficient amounts of (a) a sugar, (b) phosphate, (c) glutamic acid or a physiologically acceptable salt thereof and, optionally, (d) a non-toxic protein, a peptone or a mixture of two or more amino acids besides glutamic acid are required so that the stability of the agent in the composition is enhanced. Suitable stabilising amounts of each component are:

(a) 0.5 to 3%, preferably 0.8 to 1.5%, by weight such as about 1% by weight;

(b) 0.5 to 1.5%, preferably 0.7 to 1%, by weight such as about 0.8% by weight;

(c) 0.2 to 1%, preferably 0.3 to 0.5%, by weight such as about 0.4% by weight; and (d) 0.5 to 3%, preferably 1 to 2%, by weight such as about 1.5% by weight.

When (c) is glutamic acid, preferably a composition of the invention contains a weight ratio of (a):(b):(c): optionally (d) of about 1:0.76:0.37:0.46. This ratio especially applies when (a) is sucrose, (b) is (b') $KH_2PO_4$ and (b") $K_2HPO_4$, (c) is L-glutamic acid and (d) is human serum albumin. In this event, the preferred weight ratio of (a):(b'):(b"):(c): optionally (d) is about 1:0.40:0.36:0.37:0.46.

When (c) is sodium glutamate, preferably a composition of the invention contains a weight ratio of (a):(b):(c):

optionally (d) of about 1:0.76:0.49:0.46. This ratio especially applies when (a) is sucrose, (b) is (b') $KH_2PO_4$ and (b") $K_2HPO_4$, (c) is sodium glutamate and (d) is human serum albumin. In this event, the preferred weight ratio of (a):(b'):(b"):(c): optionally (d) is about 1:0.40:0.36:0.49:0.46.

It is believed that a synergistic effect may be operating to increase the stability of the compositions of the invention. Preferably, therefore, (a) to (c) and optionally (d) and, indeed, the $D_2O$ and (a) to (c) and optionally (d) are present in respective amounts which provide a synergistic stabilising effect.

A particularly useful composition according to the invention comprises a biological agent dissolved or dispersed in a $D_2O$ SPG or SPGA solution. $D_2O$ SPG and SPGA solutions are:

SPG solution a solution in $D_2O$ of:

1.09%, for example 1.085%, w/v sucrose, 0.43%, for example 0.432%, w/v $KH_2PO_4$, 0.39%, for example 0.392%, w/v $K_2HPO_4$, and 0.40%, for example 0.403%, w/v L-glutamic acid, or 0.53%, for example 0.539%, w/v sodium glutamate;

SPGA solution a solution in $D_2O$ of:

1.09%, for example 1.085%, w/v sucrose, 0.43%, for example 0.432%, w/v $KH_2PO_4$, 0.39%, for example 0.392%, w/v $K_2HPO_4$, 0.40%, for example 0.403%, w/v L-glutamic acid or 0.53%, for example 0.529%, w/v sodium glutamate, and 0.50% w/v human serum albumin.

A SPG solution may alternatively be defined as 0.218M sucrose, 0.0038M $KH_2PO_4$ , 0.0072M $K_2HPO_4$ and 0.0049 M monosodium glutamate in $D_2O$. Similarly, a SPGA solution may be defined as 0.218M sucrose, 0.0038M $KH_2PO_4$ , 0.0072M $K_2HPO_4$, 0.0049M monosodium glutamate and 1% by weight albumin in $D_2O$.

A composition of the invention may be a single-strength $D_2O$ SPG or SPGA solution as defined above. Alternatively, it may be above or below a single-strength solution. It may be from a half to five times single-strength, for example from one to four times single-strength. A $D_2O$ SPG or SPGA solution of variable strength may thus be present.

A composition of the invention may contain additional components. For example, a poliovirus vaccine may contain one or more antibiotics. Typically, the vaccine may contain trace amounts of polymixin and/or neomycin. The poliovirus vaccine will necessarily contain live attenuated strains of all three types of poliovirus or inactivated strains of all three types of poliovirus.

A composition of the invention is prepared according to the invention by a process which comprises dissolving or dispersing the biological agent in a $D_2O$ solution of the said amounts of the sugar, phosphate, glutamic acid or salt thereof and, optionally, non-toxic protein, peptone or mixture of two or more amino acids other than glutamic acid.

This may be achieved in any appropriate fashion. In the case where the biological agent is a poliovirus, the poliovirus is first grown in tissue culture such as in human diploid cells or monkey kidney cells. The tissue culture fluid is harvested and sterilised through a filter. Concentrates obtained in this way of poliovirus strains of each of types 1, 2 and 3 can then be blended together. Then the resulting blend is dissolved or dispersed in the $D_2O$ solution according to the invention. The $D_2O$ solution can first be sterilised, for example by passing through a sterilising filter.

The solution or dispersion obtained by the process of the invention is generally sterilised by passing through a sterilising filter. The sterilised solution or dispersion may then be dispensed into containers, glass or plastic, which are then sealed. The containers are typically unit-dose or multi-dose containers such as ampoules or vials.

These containers can be stored under appropriate conditions. Depending upon the nature of the biological agent, they may be stored at 4° to 8° C. such as in a refrigerator or at room temperature such as on the shelf. The solutions or dispersions within the containers do, however, exhibit enhanced stability and so may be stored for longer than previously under the same conditions as were used previously. Alternatively, they may not need to be stored in a refrigerator when previous solutions were so stored.

The following Examples illustrate the invention

EXAMPLE 1

Preparation of diluent solutions

Figure 1:
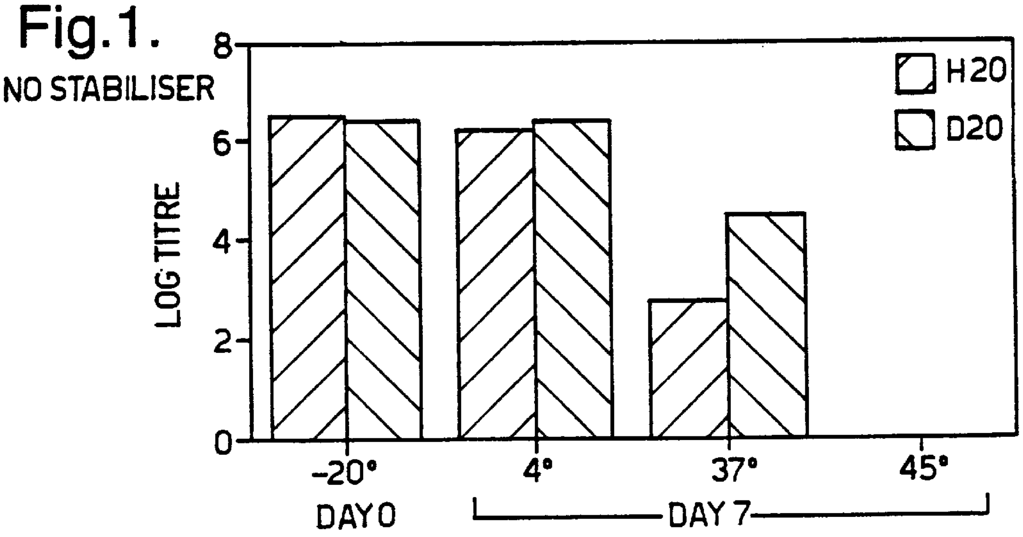
FIGS. 1, 2 and 3 are graphs of mean $\log_{10}$ titre of poliovirus in $H_2O$ and in $D_2O$ at day 0 and at day 7 when no stabiliser is added (FIG. 1), when SPGA is added as a stabiliser (FIG. 2) and when $MgCl_2$ is added as a stabiliser (FIG. 3).

The following diluent solutions were prepared. $D_2O$ was from Sigma, product no. D-4501, stated to be 99.9% D. $MgCl_2$ was from Fisons, product no. M/0600/53. Albumin was human albumin 20% B.P. (British Pharmacopoeia). No antibiotics were added to the solutions. The solutions were sterilised by passing through a sterilising filter. s.s.=single strength and 4×=four times single strength.

| (a) 4x SPG | |
|---|---|
| $KH_2PO_4$ | 0.173 g |
| $K_2HPO_4$ | 0.157 g |
| Sucrose | 0.434 g |
| L-Glutamic acid | 0.161 g |
| Water for Injections (WFI) or $D_2O$ | to 10 ml |
| (b) s.s. SPGA | |
| $KH_2PO_4$ | 0.432 g |
| $K_2HPO_4$ | 0.392 g |
| Sucrose | 1.085 g |
| L-Glutamic acid | 0.403 g |
| Albumin (added after pH adjustment and sterilisation) | 7.5 ml |
| WFI or $D_2O$ | to 100 ml |

4M KOH was added to adjust the pH to 6.6.

(c) 1M $MgCl_2$ 20.3 g of $MgCl_2$. $6H_2O$ was dissolved in 100 ml of WFI or $D_2O$ (d) 3M $MgCl_2$ 6.1 g of $MgCl_2$. $6H_2O$ was dissolved in 10 ml of WFI

EXAMPLE 2

Preparation of Formulations

Formulations of poliovirus type 3 Sabin strain were prepared. A target titre of $10^{6.1}$ per 0.15 ml dose was required which corresponded to a titre of $10^{6.92}$ per ml. A batch of the poliovirus was grown in human diploid cells in culture to a titre of approximately $10^{8.0}$. The culture was sterilised by passing through a sterilising filter. The following formulations were prepared:

| Formulation | Formula | ml/100ml |
|---|---|---|
| 1. No Stabiliser | Type III virus | 8.3 |
| | WFI | 91.7 |
| 2. No Stabiliser + $D_2O$ | Type III virus | 8.3 |
| | WFI | 7.7 |
| | $D_2O$ | 84.0 |
| 3. SPGA | Type III virus | 8.3 |
| | 4xSPG (made in WFI) | 2.8 |
| | Albumin | 0.8 |
| | s.s. SPGA (made in WFI) | 88.1 |
| 4. SPGA + $D_2O$ | Type III virus | 8.3 |
| | 4xSPG (made in $D_2O$) | 2.8 |
| | Albumin | 0.8 |
| | s.s. SPGA (made in $D_2O$) | 88.1 |
| 5. $MgCl_2$ | Type III virus | 8.3 |
| | 3M $MgCl_2$ (made in WFI) | 4.2 |
| | 1M $MgCl_2$ (made in WFI) | 87.5 |
| 6. $MgCl_2$ + $D_2O$ | Type III virus | 8.3 |
| | 3M $MgCl_2$(made in WFI) | 4.2 |
| | 1M $MgCl_2$ (made in WFI) | 3.5 |
| | 1M $MgCl_2$ (made in $D_2O$) | 84.01 |

Formulations 3 and 4 were in fact single strength SPGA. Thorough mixing of the blends was ensured with minimum agitation. Solutions containing $D_2O$ were opened to the air for as short a time as possible to prevent exchange with hydrogen ions from atmospheric $H_2O$. For each formulation, the solutions were mixed in the order indicated in the Table. Using an Eppendorf repeater pipette fitted with a 50 ml syringe filler, the formulations were aliquoted into 1 ml samples in bijou bottles, 80 samples per formulation. Each of the formulations was sampled at day 0 and stored at 4° C., 37° C. and 45° C. for sampling on future days as below:

| Temperature | Day | No. of replicates |
|---|---|---|
| | 0 | 8 |
| 4° C. | 1 | 8 |
| | 2 | 8 |
| | 7 | 8 |
| 37° C. | 1 | 8 |
| | 2 | 8 |
| | 7 | 8 |
| 45° C. | 1 | 8 |
| | 2 | 8 |
| | 7 | 8 |

The samples were then kept at −20° C. until ready for analysis. Virus titres were determined by an Infectivity Titre test. The Infectivity Titre test complies with WHO TRS800. The results are as follows:

Day 0

| Sample Description | Total Virus Content ($TCID_{50}$/ml) | Mean Titre (95% Fiducial Limits) |
|---|---|---|
| 1. No Stabiliser | $10^{7.02}$, $10^{6.57}$, $10^{6.44}$ * | $10^{6.50}$ ($10^{6.32}$ − $10^{6.68}$) |
| 2. No Stabiliser + $D_2O$ | $10^{6.58}$, $10^{6.33}$, $10^{6.39}$ * | $10^{6.42}$ ($10^{6.28}$ − 106.56) |
| 3. SPGA | $10^{7.19}$ , $10^{6.94}$, $10^{7.04}$ | $10^{7.07}$ ($10^{6.94}$ − $10^{7.19}$) |
| 4. SPGA + $D_2O$ | $10^{7.02}$, $10^{6.96}$, $10^{7.02}$ | $10^{7.00}$ ($10^{6.86}$ − $10^{7.15}$) |
| 5. $MgCl_2$ | $10^{6.86}$, $10^{6.81}$, $10^{6.93}$ | $10^{6.85}$ ($10^{6.71}$ − $10^{6.99}$) |

-continued

| Sample Description | Total Virus Content ($TCID_{50}$/ml) | Mean Titre (95% Fiducial Limits) |
|---|---|---|
| 6. $MgCl_2$ + $D_2O$ | $10^{7.01}$, $10^{6.81}$, $10^{6.86}$ | $10^{6.89}$ ($10^{6.75}$ − $10^{7.03}$) |
| Type III Standard | $10^{8.12}$, $10^{8.21.}$ $10^{8.05}$ | $10^{8.13}$ ($10^{7.99}$ − $10^{8.27}$) |

*Outside limits

| Sample Description | Total Virus Content ($TCID_{50}$/ml) | | Mean Titre (95% Fiducial Limits) |
|---|---|---|---|
| Day 7 at 4° C. | | | |
| 1. No Stabiliser | $10^{6.19}$ | $10^{6.19}$ | $10^{6.19}$ ($10^{6.00}$ − $10^{6.38}$) |
| 2. No Stabiliser + $D_2O$ | $10^{6.45}$ | $10^{6.28}$ | $10^{6.37}$ ($10^{6.15}$ − $10^{6.58}$) |
| 3. SPGA | $10^{7.01}$ | $10^{7.06}$ | $10^{7.04}$ ($10^{6.86}$ − $10^{7.21}$) |
| 4. SPGA + $D_2O$ | $10^{6.96}$ | $10^{7.14}$ | $10^{7.04}$ ($10^{6.89}$ − $10^{7.19}$) |
| 5. $MgCl_2$ | $10^{6.97}$ | $10^{6.96}$ | $10^{6.96}$ ($10^{6.80}$ − $10^{7.14}$) |
| 6. $MgCl_2$ + $D_2O$ | $10^{7.01}$ | $10^{6.95}$ | $10^{6.98}$ ($10^{6.80}$ − $10^{7.16}$) |
| Type III Standard | $10^{8.08}$ | $10^{8.13}$ | $10^{8.11}$ ($10^{7.95}$ − $10^{8.28}$) |
| Day 7 at 37° C. | | | |
| 1. No Stabiliser | $10^{2.67}$ | $10^{2.87}$ | $10^{2.77}$ ($10^{2.59}$ − $10^{2.95}$) |
| 2. No Stabiliser + $D_2O$ | $10^{4.33}$ | $10^{4.64}$ | $10^{4.49}$ ($10^{4.33}$ − $10^{4.64}$) |
| 3. SPGA | $10^{6.00}$ | $10^{6.06}$ | $10^{6.03}$ ($10^{5.86}$ − $10^{6.20}$) |
| 4. SPGA + $D_2O$ | $10^{6.65}$ | $10^{6.58}$ | $10^{6.61}$ ($10^{6.44}$ − $10^{6.78}$) |
| 5. $MgCl_2$ | $10^{5.88}$ | $10^{5.92}$ | $10^{5.91}$ ($10^{5.75}$ − $10^{6.06}$) |
| 6. $MgCl_2$ + $D_2O$ | $10^{6.13}$ | $10^{6.07}$ | $10^{6.09}$ ($10^{5.92}$ − $10^{6.26}$) |
| Type III Standard | $10^{8.08}$ | $10^{8.13}$ | $10^{8.11}$ ($10^{7.95}$ − $10^{8.28}$) |
| Day 7 at 45° C. | | | |
| 1. No Stabiliser | No viable poliovirus | | |
| 2. No Stabiliser + $D_2O$ | No viable poliovirus | | |
| 3. SPGA | No viable poliovirus | | |
| 4. SPGA + $D_2O$ | $10^{4.81}$ | $10^{4.77}$ | $10^{4.79}$ ($10^{4.62}$ − $10^{4.97}$) |
| 5. $MgCl_2$ | No viable poliovirus | | |
| 6. $MgCl_2$ + $D_2O$ | $10^{3.51}$ | $10^{3.32}$ | $10^{3.42}$ ($10^{3.20}$ − $10^{3.64}$) |
| Type III Standard | $10^{8.08}$ | $10^{8.13}$ | $10^{8.11}$ ($10^{7.95}$ − $10^{8.28}$) |

The results can be summarised as follows:

| Mean | No Stabiliser | | SPGA | | $MgCl_2$ | |
|---|---|---|---|---|---|---|
| Titre | $-D_2O$ | $+D_2O$ | $-D_2O$ | $+D_2O$ | $-D_2O$ | $+D_2O$ |
| Day 0 | $10^{6.50}$ | $10^{6.42}$ | $10^{7.07}$ | $10^{7.00}$ | $10^{6.85}$ | $10^{6.89}$ |
| Day 7 4° C. | $10^{6.19}$ | $10^{6.37}$ | $10^{7.04}$ | $10^{7.04}$ | $10^{6.96}$ | $10^{6.98}$ |
| Day 7 37° C. | $10^{2.77}$ | $10^{4.49}$ | $10^{6.08}$ | $10^{6.61}$ | $10^{5.91}$ | $10^{6.09}$ |
| Day 7 45° C. | None detected | None detected | None detected | $10^{4.79}$ | None detected | $10^{3.42}$ |

Figure 2:
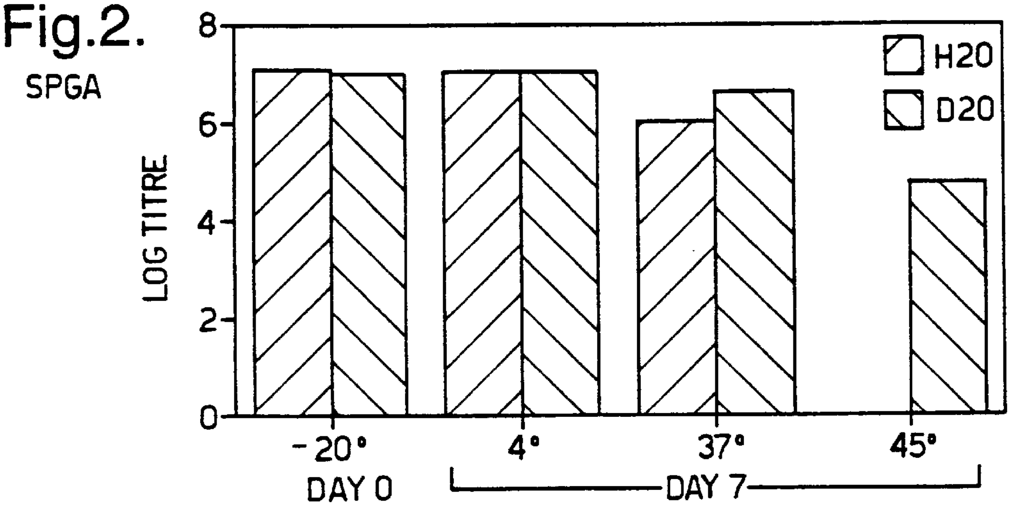
Figure 3:
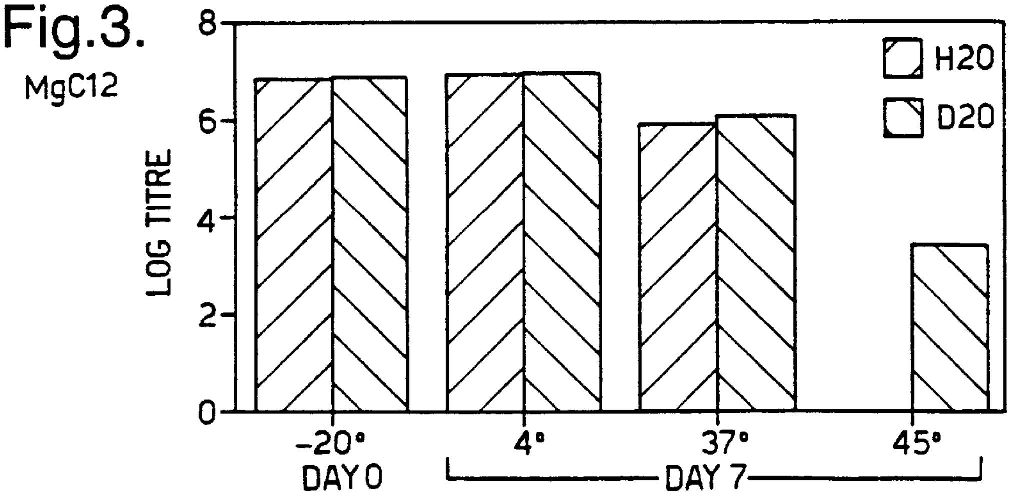

These results are represented graphically in FIGS. 1, 2 and 3 of the accompanying drawings. The initial titre of the Day 0 No Stabiliser formulation was low. This may have been due to the time that the virus stock stood at room temperature prior to blending. The target titre of $10^{6.92}$/ml was achieved at 4° C. after 7 days for the SPGA and $MgCl_2$ blends but not for the blend with No Stabiliser. At the higher temperatures of 37° C. and 45° C., the addition of $D_2O$ to the samples improved the stability of the virus. The loss in titre is expressed below as a logarithmic percentage of the initial antigen content:

| $Log_{10}$ | No Stabiliser | | SPGA | | $MgCl_2$ | |
|---|---|---|---|---|---|---|
| Titre | $-D_2O$ | $+D_2O$ | $-D_2O$ | $+D_2O$ | $-D_2O$ | $+D_2O$ |
| Day 0 | 6.50 | 6.42 | 7.07 | 7.00 | 6.85 | 6.89 |
| Day 7 | | | | | | |
| 4° C. | 6.19 | 6.37 | 7.04 | (7.04) | (6.96) | (6.98) |
| Loss % | 51% | 11% | 7% | (10%) | (29%) | (23%) |
| Day 7 | | | | | | |
| 37° C. | 2.77 | 4.49 | 6.03 | 6.61 | 5.91 | 6.09 |
| Loss % | 100% | 99% | 91% | 59% | 89% | 84% |
| Day 7 | Not | Not | Not | 4.79 | Not | 3.42 |
| 45° C. | Det. | Det. | Det. | 99% | Det. | 100% |
| Loss % | 100% | 100% | 100% | | 100% | |

All percentages have been rounded up to the nearest whole number, hence the apparent 100% loss even where some antigen is detected. The figures in brackets were higher than the initial (Day 0) titre. This apparent increase was due to the variability of the assay. The results emphasise the superiority of the formulations containing both SPGA and $D_2O$.

We claim:

1. A vaccine which comprises a suspension of a virus in a diluent, wherein the diluet comprises (1) $D_2O$ as the principal component and (2) (a) a sugar, (b) phosphate, (c) glutamic acid or a physiologically acceptable salt thereof, and optionally (d) a non-toxic protein, a peptone or a mixture of two or more amino acids besides glutamic acid, components (1) and (2) being present in amounts that enhance the stability of the virus.

2. The vaccine according to claim 1, which comprises a live attenuated poliovirus or an inactivated poliovirus of each of poliovirus types 1, 2 and 3.

3. The vaccine according to claim 1 or 2, wherein the diluent comprises (a) from 0.5 to 3% by weight of sugar, (b) from 0.5 to 1.5% by weight of phosphate, (c) from 0.2 to 1% by weight of glutamic acid or sodium glutamate, and optionally (d) from 0.5 to 3% by weight of the non-toxic protein, peptone or said mixture of amino acids.

4. The vaccine according to claim 1 or 2, wherein the diluent comprises (a) sucrose as the sugar, (b') $KH_2PO_4$ and (b") $K_2HPO_4$ as the phosphate, (c) L-glutamic acid or sodium glutamate, and optionally (d) human serum albumin as the non-toxic protein in a weight ratio of (a):(b'):(b"):(c): optionally (d) of about 1:0.40:0.36:0.37:0.46 when (c) is glutamic acid or about 1:0.40:0.36:0.49:0.46 when (c) is sodium glutamate.

5. The vaccine according to claim 1 or 2, wherein the suspension comprises the virus and a $D_2O$ SPG or SPGA solution as follows:

SPG a solution in $D_2O$ of:

1.09% w/v sucrose, 0.43% w/v $KH_2PO_4$, 0.39% w/v $K_2HPO_4$, and 0.40% w/v L-glutamic acid or 0.53% w/v sodium glutamate;

SPGA a solution in $D_2O$ of:

1.09% w/v sucrose, 0.43% w/v $KH_2PO_4$, 0.39% w/v $K_2HPO_4$, 0.40% w/v L-glutamic acid or 0.53% w/v sodium glutamate, 0.50% w/v human serum albumin.

6. The vaccine according to claim 1 or 2 wherein the phosphate (b) buffers the suspension to a pH at which the virus is stable.

7. A process for the preparation of a vaccine, which process comprises forming a suspension of a virus in a diluent comprising (1) $D_2O$ as the principal component and (2) (a) sugar, (b) phosphate, (c) glutamic acid or a physiologically acceptable salt thereof, and optionally (d) a non-toxic protein, a peptone or a mixture of two or more amino acids besides glutamic acid, components (1) and (2) being present in amounts that enhance the stability of the virus.

8. The process according to claim 7, wherein the suspension of virus in diluent is sterilized by passing through a sterilizing filter and dispensed into unit- or multi-dose containers which are then sealed.

9. The process according to claim 7, wherein the virus is a live attenuated poliovirus or an inactivated poliovirus of each of poliovirus types 1, 2 and 3.

10. The process according to claim 7, wherein the diluent comprises (a) from 0.5 to 3% by weight of sugar, (b) from 0.5 to 1.5% by weight of phosphate, (c) from 0.2 to 1% by weight of glutamic acid or sodium glutamate, and optionally (d) from 0.5 to 3% by weight of the non-toxic protein, peptone or said mixture of amino acids.

11. The process according to claim 7, wherein the diluent comprises (a) sucrose as the sugar, (b') $KH_2PO_4$ and (b") $K_2HPO_4$ as the phosphate, (c) L-glutamic acid or sodium glutamate, and optionally (d) human serum albumin as the non-toxic protein in a weight ratio of (a):(b'):(b"):(c): optionally (d) of about 1:0.40:0.36:0.37:0.46 when (c) is glutamic acid or about 1:0.40:0.36:0.49:0.46 when (c) is sodium glutamate.

12. The process according to claim 7, wherein the diluent is a $D_2O$ SPG or SPGA solution as follows:

SPG a solution in $D_2O$ of:

1.09% w/v sucrose, 0.43% w/v $KH_2PO_4$, 0.39% w/v $K_2HPO_4$, and 0.40% w/v L-glutamic acid or 0.53% w/v sodium glutamate;

SPGA a solution in $D_2O$ of:

1.09% w/v sucrose, 0.43% w/v $KH_2PO_4$, 0.39% w/v $K_2HPO_4$, 0.40% w/v L-glutamic acid or 0.53% w/v sodium glutamate, 0.50% w/v human serum albumin.

* * * * *